United States Patent [19]

Cartmell et al.

[11] Patent Number: 5,195,523
[45] Date of Patent: Mar. 23, 1993

[54] MEDICAL ELECTRODE ASSEMBLY

[75] Inventors: James V. Cartmell, Xenia; Joseph F. DeRosa, Centerville; Jeffrey W. Stone, Cincinnati, all of Ohio

[73] Assignee: NDM Acquisition Corp., Minneapolis, Minn.

[21] Appl. No.: 690,868

[22] Filed: Apr. 24, 1991

[51] Int. Cl.⁵ .............................................. A61B 5/0402
[52] U.S. Cl. ..................................... 128/640; 128/798; 128/802; 439/86; 439/729; 439/909
[58] Field of Search .............. 128/639, 640, 798, 802, 128/803; 606/32; 439/86, 506, 729, 835–838, 909

[56] References Cited

U.S. PATENT DOCUMENTS

| | | |
|---|---|---|
| 3,976,055 | 8/1976 | Monter et al. |
| 4,178,052 | 12/1979 | Ekbom et al. ............... 439/729 X |
| 4,257,424 | 3/1981 | Cartmell . |
| 4,268,101 | 5/1981 | Stone ............................. 439/86 |
| 4,617,935 | 10/1986 | Cartmell et al. |
| 4,635,642 | 1/1987 | Cartmell et al. |
| 4,643,193 | 2/1987 | De Marzo . |
| 4,653,501 | 3/1987 | Cartmell et al. |
| 4,674,511 | 6/1987 | Cartmell . |
| 4,699,679 | 10/1987 | Cartmell et al. |
| 4,721,111 | 1/1988 | Muttitt . |
| 4,722,761 | 2/1988 | Cartmell et al. |
| 4,727,880 | 3/1988 | Roberts . |
| 4,727,881 | 3/1988 | Craighead et al. |
| 4,773,424 | 9/1988 | Inoue et al. |
| 4,797,125 | 1/1989 | Malana ......................... 128/639 X |
| 4,827,939 | 5/1989 | Cartmell et al. |
| 4,832,036 | 5/1989 | Cartmell . |
| 4,852,571 | 8/1989 | Gadsby et al. |
| 4,893,626 | 1/1990 | Henley et al. |
| 4,915,656 | 4/1990 | Alferness . |
| 4,926,878 | 5/1990 | Snedeker . |
| 4,934,049 | 6/1990 | Kiekhafer et al. |
| 4,934,367 | 6/1990 | Daglow et al. ................ 439/86 X |
| 4,945,911 | 8/1990 | Cohen et al. |
| 5,012,810 | 5/1991 | Strand et al. |
| 5,058,589 | 10/1991 | Ding et al. |

FOREIGN PATENT DOCUMENTS

3307896 9/1984 Fed. Rep. of Germany ...... 128/640

Primary Examiner—Lee S. Cohen
Attorney, Agent, or Firm—Killworth, Gottman, Hagan & Schaeff

[57] ABSTRACT

A medical electrode assembly for an electrocardiograph or similar device is provided. The medical electrode assembly comprises an electrolyte pad having an electrolyte layer which may be secured to the skin of a patient and a backing member made from a nonconductive material being coextensively superposed directly onto the electrolyte layer. The electrolyte pad is used in conjunction with a reusable lead wire connector having at least one surface contacting the electrolyte layer of the electrolyte pad. The reusable lead wire connector includes a set of jaws which may be compressed together for contacting the electrolyte pad. The set of jaws may be formed of a nonconductive binder material having a conductive filler dispersed therein. A metallic conductive material, such as a silver/silver chloride system, is superposed over the nonconductive binder material.

3 Claims, 4 Drawing Sheets

MEDICAL ELECTRODE ASSEMBLY

BACKGROUND OF THE INVENTION

The present invention generally relates to a medical electrode assembly, and more particularly, to an electrolyte pad used in conjunction with a reusable lead wire connector for an electrocardiograph or similar monitoring equipment.

Medical electrodes of the foregoing type are utilized in a number of applications for a variety of purposes. The monitoring of physiological electric potentials to detect muscular activity of the heart muscle is generally well established, such apparatus being referred to in the art as electrocardiograph (also referred to herein as ECG) apparatus. The resulting traces derived from such apparatus provide a diagnostic tool for detecting heart disease and/or defects. Such monitoring of physiological electrical potentials may be employed in a number of other applications. However, the medical electrode and reusable lead wire connector of the present invention will be described herein with reference to its connection with ECG apparatus.

Such ECG traces may be desired in a number of different situations. For example, a simple ECG test to obtain a single tracing for diagnostic purposes may be carried out in a few minutes in a physician's office. Hence, medical electrodes utilized for such testing may be of a relatively simple disposable variety, since they are only in service for a very short time. Conversely, longer term monitoring applications require that the medical electrodes remain in place on the patient's skin for considerably extended periods of time. For example, in stress testing, the heart activity of the patient is monitored over a relatively longer period of time while the patient exercises upon a tread mill or similar apparatus. Such testing may include monitoring of the heart activity during the exercise, as well as continued monitoring during the rest period thereafter so as to monitor the return of the heart to a normal or unstressed condition. Similarly, medical electrodes monitoring heart activity during surgery may be required to remain in place and operational for a period of several hours. In a similar fashion, patients hospitalized in an intensive care ward or other specialized care unit may require continuous monitoring. Hence, medical electrodes utilized for ECG monitoring over such extended periods must remain in service for many hours and sometimes for many days.

Accordingly, there is a continuing need for high quality yet inexpensive medical electrodes for ECG and related uses which reliably transmit signals to enable traces to be obtained that accurately represent signals generated by the patient's heart. For purposes of convenience and safety, such medical electrodes should be so inexpensive that it is practical to dispose of them after only one use. In the past, an approach to providing inexpensive ECG medical electrodes has been to provide a disposable medical electrode which includes an electrolyte and a conductor engaged therein. For example, U.S. Pat. Nos. 4,773,424, 4,257,424, 4,643,193, 4,721,111 and 4,727,881 are all directed to disposable medical electrodes having an electrolyte and a conductor engaged therein.

It is generally recognized that, in order to obtain high quality traces, the portion of the electrode conductor engaged in the electrolyte should be substantially pure metal, preferably either substantially pure silver or a silver coated conductive plastic. When pure metallic silver is used, the electrolyte will contain a chloride ion, thus forming a conductor coating commonly referred to in the art as a silver/silver chloride system. Such silver/silver chloride systems are necessary for providing a regular electrocardiograph trace having a stable base line. The silver/silver chloride system eliminates the erratic traces and wandering base lines sometimes attributed to defibrillation. However, the silver/silver chloride system is extremely expensive when compared to the costs associated with the other components of the medical electrode. Therefore, the conductor portion of medical electrodes usually comprise the most expensive part of the medical electrode. There have been many attempts in the past to minimize the expense associated with silver/silver chloride systems used in medical electrodes.

For example, U.S. Pat. No. 4,674,511 (commonly assigned) discloses a medical electrode for ECG monitoring which includes a conductor member comprising a thin strip of nonconductive material having a thin layer of electrically conductive paintable material adhered to one face thereof. By including only a thin strip of electrically conductive material on the medical electrode, the expense associated with such electrically conductive materials is minimized. However, the disposable medical electrode disclosed in U.S. Pat. No. 4,674,511 does in fact include the expensive electrically conductive material as a component and therefore, is discarded with the medical electrode. The disposition of the electrically conductive material increases the expense of using the disposable medical electrode.

As a response to such problems, attempts in the art have sought to provide a medical electrode having a reusable conductor portion. These medical electrodes typically comprise a disposable portion and a reusable conductor portion. For example, U.S. Pat. No. 4,653,501 (commonly assigned) discloses a medical electrode with a reusable conductor comprising a disposable electrode pad with a socket for receiving a reusable electrode conductor which is attached to a lead wire. The pad includes a socket plate having a release coated top surface and a bore filled with a gel matrix which serves as the electrolyte contacting the patient's skin. In use, the medical electrode is applied to the skin of the patient and the releasable part of the clamp plates is peeled away from the socket plate, the electrode conductor is then inserted into the bore of the socket plate and the clamp is readhered to the socket plate in a covering relationship. The lead wire is then attached to the end such that the end of the lead wire and the electrode conductor are securely held in place relative to the electrolyte gel matrix.

Another attempt to minimize the expense of the medical electrode by incorporating a reusable conductor is disclosed in U.S. Pat. No. 4,635,642 (commonly assigned). The medical electrode comprises an electrode pad provided with a socket and a reusable electrode conductor which is attached to a lead wire. The electrode pad includes a laminated assembly of a pair of foamed sheets with an electrolyte gel matrix filling the gap between the foam sheets. An electrically nonconductive socket plate is disposed over the gel matrix and the foam sheets. The socket plate is provided with a socket or bore for receiving the reusable electrode conductor. The reusable electrode conductor has a ridged body slightly larger than the bore such that the bore resiliently engages the conductor. While these medical electrode assemblies may incorporate a reusable conductor, they are relatively expensive to manufacture in view of their complex structure as compared to other medical electrodes. Accordingly, medical electrodes having reusable conductors require a relatively sophisticated manufacturing scheme which significantly increase the cost of each medical electrode. Such costs substantially negate any savings associated with the reusable conductor feature.

Accordingly, there remains a need in the art for a medical electrode assembly having a simple structure which is relatively inexpensive to manufacture; there is also a need for such a medical electrode assembly which eliminates the expensive metallic conductive materials from the disposable portion of the medical electrode assembly so as to decrease the costs associated with use.

SUMMARY OF THE INVENTION

The present invention meets the aforementioned needs by providing a medical electrode assembly requiring less expensive materials and which may be inexpensively manufactured. The medical electrode assembly according to the invention is used to interconnect the lead wire from an electrocardiograph or similar device and the patient. The medical electrode assembly comprises a disposable electrolyte pad and a reusable lead wire connector. The electrolyte pad is secured to the skin of a patient requiring monitoring and serves to conduct the electrical signal between the patient's skin and the reusable lead wire connector. The reusable lead wire connector has several functions. For example, the reusable lead wire connector serves as the electrode sensor or conductor and as the lead wire interconnecting the electrocardiograph and the electrode sensor with the electrolyte pad. Additionally, the reusable lead wire connector houses the electrode sensor or conductor. The combination of the disposable electrolyte pad and reusable lead wire connector, defined herein as the medical electrode assembly, performs the medical electrode function of serving as a transducer between ionic and electric current flow. In this way, the reusable lead wire connector, which may be configured in substantially an alligator-type clip having a set of jaws, is attached to the electrolyte pad to provide a conductive path for the minute voltages generated by the patient's heart to the electrocardiograph. The medical electrode assembly of the present invention provides a regular trace having a stable base line.

The disposable electrolyte pad of the present invention comprises an electrolyte layer which is secured to the skin of a patient and a backing member being continually and coextensively superposed directly onto the electrolyte layer. The electrolyte layer and the backing member together include a tab for receiving the reusable lead wire connector. The backing member is preferably made from a nonconductive material and will have the same geometric shape as the electrolyte layer. In another aspect of the present invention, an electrolyte pad especially suitable for long-term electrocardiograph monitoring is provided. The electrolyte pad includes a backing member which has a portion extending beyond the electrolyte layer such that the extended portion may be secured to the skin of a patient. The electrolyte layer is formed of materials selected from the group consisting of conductive adhesives while the backing member is formed from a nonconductive material selected from the group consisting of polyethylene terephthalate, polystyrene, polyvinylchloride, and polyethylene.

The medical electrode assembly of the present invention further comprises a reusable lead wire connector having a set of jaws each having an inner surface which may be compressed together for contacting the tab of the electrolyte pad. A vanishingly small amount of an metallic conductive material comprising at least one metal particle is superposed directly onto the inner surface of at least one jaw. The metal particle(s) may be silver as found in the silver/silver chloride system. The preferable reusable lead wire connector will have a jaw comprising a nonconductive binder material having a conductive filler dispersed therein. The reusable lead wire connector may have a multitude of configurations including an alligator-type clip having two jaws for contacting the electrolyte pad. Alternatively, the jaws of the reusable lead wire connector may be formed of a metal while a set of inserts or sleeves are superposed over the inner surface of each jaw. The inserts or sleeves are formed from a nonconductive binder material having a conductive filler dispersed therein. A metallic conductive material, such as a metal particle, is superposed over the surface of the insert or sleeve which contacts the electrolyte pad.

A major portion of the cost savings arise by virtue of the reusable lead wire connector including as a component the relatively expensive metallic conductive material. In the past, the disposable portion of the medical electrode included the metallic conductive material, such as the silver/silver chloride system, which was discarded after a single use. This significantly added to the cost of using each medical electrode assembly. As stated above, past attempts in the art rendered the conductor or sensor portion of the medical electrode reusable as a means for reducing the costs. However, these medical electrodes are quite expensive to produce and require a relatively sophisticated manufacturing scheme. The present invention provides a simplistic solution by incorporating the conductive material into the reusable lead wire connector, thereby eliminating the expensive metallic conductive material from the disposable portion of the medical electrode.

Accordingly, it is an object of the present invention to provide an inexpensive medical electrode assembly which produces a regular trace having a stable base line; it is also an object of the present invention to provide a medical electrode assembly which minimizes costs associated with the disposable portion of the assembly. Other objects and advantages of the invention will be apparent from the following description, the accompanying drawings and the appended claims.

DETAILED DESCRIPTION OF THE PREFERRED EMBODIMENT

Figure 1:
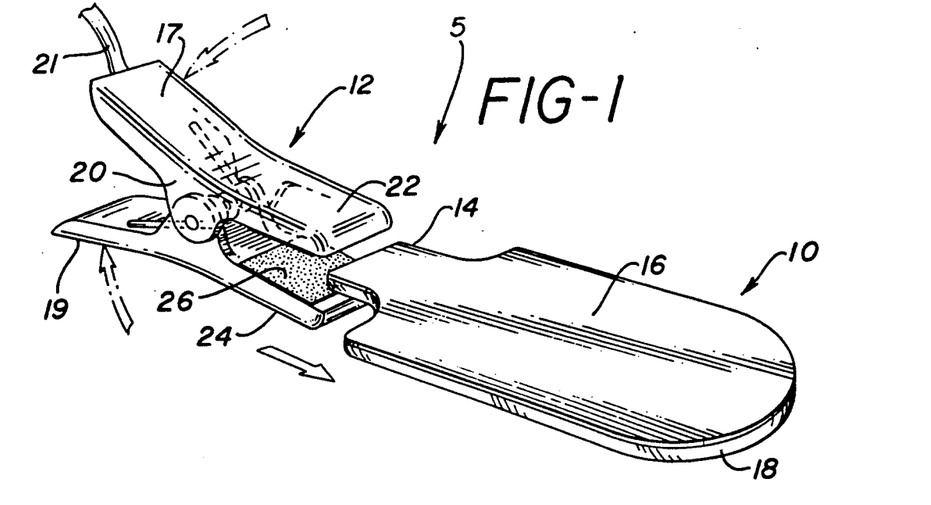
FIG. 1 is a perspective view of a medical electrode assembly in accordance with the invention.

Referring now to FIG. 1, a medical electrode assembly 5 which comprises an electrolyte pad 10 and a reusable lead wire connector 12 is shown in accordance with the invention. The electrolyte pad 10 may be secured directly to the skin of a patient requiring electrocardiograph monitoring. The reusable lead wire connector 12 is configured in substantially an alligator-type clip connector, however, it should be appreciated that other devices beyond the alligator-type clip connector may be used in accordance with the present invention. The reusable lead wire connector 12 is attached to a tab 14 which forms a portion of the electrolyte pad 10. A lead wire 21 connecting the reusable lead wire connector 12 to the electrocardiograph or similar monitoring equipment provides a path for the minute voltages generated by the heart of the patient to the electrocardiograph. The result is an electrocardiograph trace which may used for diagnostic purposes. As discussed above, medical electrodes of the past produced an erratic trace with a wandering base line which made it difficult to ascertain the requisite diagnostic information from the trace. Many recent disposable medical electrodes incorporate relatively expensive metallic conductive materials, such as the aforedescribed silver/silver chloride system, at the interface between the electrode conductor or sensor portion and the electrolyte of the medical electrode.

However, as can be seen in FIG. 1, the disposable electrolyte pad 10 does not include the metallic conductive material in the disposable portion of the medical electrode assembly 5. Rather, the electrolyte pad 10 comprises a backing member 16 being coextensively superposed directly onto an electrolyte layer 18. Preferably, the backing member 16 is made from a nonconductive material selected from the group consisting of polyethylene terephthalate (commercially available from E. I. DuPont de Nemours & Co. under the trademark Mylar ®), polystyrene, polyethylene, polypropylene and polyvinylchloride. The most preferable nonconductive material is polyethylene. Additionally, a carrier or release sheet (not shown) may be used to protect and store the electrolyte pad prior to use. Such carrier sheets are widely known and used in the art.

The electrolyte layer 18 is preferably selected from the group consisting of conductive adhesives. When the electrolyte layer 18 is formed from a conductive adhesive, such as hydrogel, it must have adhesive properties to facilitate adherence to the patient's skin. The preferred conductive adhesives are commercially available, for example, from LecTec Corp., Conductive Adhesive Membrane TM (product #LT-4000) and from Promeon, Div. of Medtronic, Inc., Promeon Hydrogel TM (product #RG-63B). A multitude of other electrolytic materials known in the art may be used in accordance with the invention. The material used to form the electrolyte layer 18 must be compatible with the patient's skin as it is secured directly to the skin of the patient.

The material of choice for the electrolyte layer 18 contains an electrolyte in an amount sufficient to render it ionically conductive. In this regard, the material may include an ionizable salt which is compatible with the metal used in the reusable lead wire connector 12 of the medical electrode assembly 5. The combination of an ionizable salt and a metal which are compatible with one another such that they function as an electrode are well known in the art. For example, an ionic solution of sodium chloride is used with silver metal to serve as the silver/silver chloride system, which is preferred with the present invention. Alternatively, sodium sulfate may be used with stainless steel. It will be appreciated by those skilled in the art that other materials may be used to form the backing member 16 and the electrolyte layer 18 in addition to those described herein. The backing member 16 and the electrolyte layer 18 together which form the electrolyte pad 10 preferably are coextensive. In that regard, any shape which is compatible with the patient and the electrocardiograph may used in accordance with the invention. For example, the electrolyte pad 10 may have substantially an oval, circular, square or rectangular shape. However, it is preferable that the shape of choice includes the tab 14 which provides a means for receiving the reusable lead wire connector 12.

Figure 2:
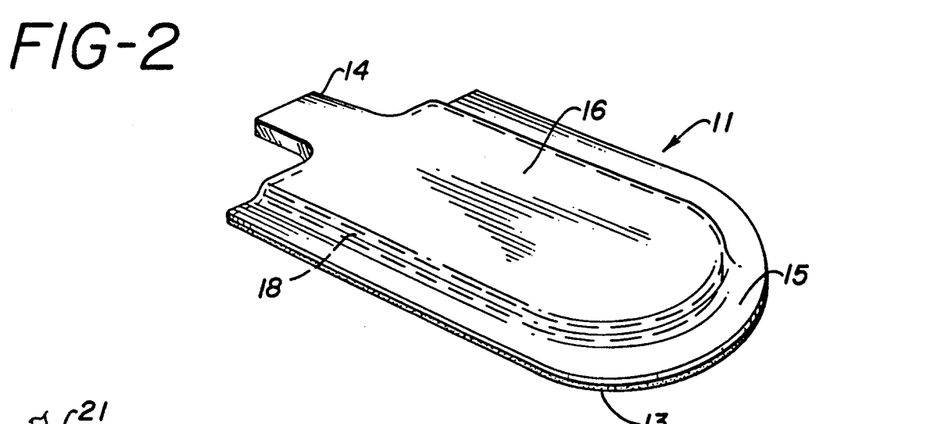
FIG. 2 is a perspective view of an electrolyte pad which is especially suitable for long-term monitoring of a patient.

Referring now to FIG. 2, another embodiment of the present invention is illustrated. An electrolyte pad 11 includes a backing member 16 and an adhesive layer 13 together having a portion 15 extending outwardly beyond the periphery of the electrolyte layer 18 so that the portion 15 may be adhesively secured to the skin of the patient. This particular embodiment of the medical electrode assembly 5 is especially useful for long-term monitoring of the patient. It should be noted that the portion 15 does not extend beyond the periphery of the tab 14. Preferably, the adhesive layer 13 comprises a nonconductive pressure sensitive adhesive of the type generally known as "patient contact" adhesives which may affix safely the electrolyte pad 11 to the skin of the patient.

In regard to the relative dimensions of the electrolyte pad 10 as depicted in FIGS. 1 and 2, the thickness of the electrolyte layer 18 and the backing member 16 must be sufficient so as to provide a path for the voltages generated by the patient's heart to the electrocardiograph with a minimum amount of interface impedance. Preferably, the thickness of the backing member 16 will be in a range from approximately 0.01 mm to 0.25 mm and the electrolyte layer 18 will be in a range from approximately 0.25 mm to 3.175 mm. More preferably, the thickness of the backing member 16 will be in range approximately from 0.025 mm to 0.125 mm and the electrolyte layer 18 will be in a range from approximately 0.50 mm to 1.60 mm. The relative dimensions of the electrolyte pad 10 may vary depending upon the particular application and the chosen shape.

Thus, the electrolyte pad 10 according to the present invention does not include a metallic conductive material deposited therein. Accordingly, the electrolyte pad 10 may be disposed after use without also disposing the relatively expensive metallic conductive material such as those materials used in the silver/silver chloride system. This enormously reduces the expense of the medical electrode assembly 5. Moreover, the medical electrode assembly 5 has a relatively simple construction having a lower unit cost as compared to other medical electrodes used in the industry. In accordance with the invention, the reusable lead wire connector 12 houses the conductor or sensor portion of the medical electrode assembly 5. Thus, the reusable lead wire connector 12 also includes the metallic conductive material designated by reference numeral 26. This is of major significance in that the reusable lead wire connector 12 is reusable, thereby eliminating the disposition of the expensive metallic conductive material 26 after only a single use. This significantly reduces the costs associated with using the medical electrode assembly 5. Those skilled in the art will appreciate that the reusable lead wire connector 12 designs illustrated and described herein are by example only, and that a variety of other reusable lead wire connector designs may be used in accordance with the present invention.

As can be seen in FIG. 1, one embodiment of the invention includes a reusable lead wire connector 12 comprising an alligator-type body 20 having two jaws 22 and 24 which remain compressed together. A pair of handles 17 and 19 of the alligator-type body 20 may be compressed which thereby pulls the two jaws 22 and 24 apart such that the reusable lead wire connector 12 may be secured to the tab 14 of the medical electrode assembly 5. At least one of the two jaws 22 and 24 will have the conductive material 26 deposited thereon. Preferably, the conductive material 26 comprises at least one metal particle which is superposed over the inner surface of at least one of the two jaws 22 and 24. More preferably, a layer of metal particles will be formed on the surface of each jaw 22 and 24. The conductive material 26 is preferably formed from a metal selected from the group consisting of titanium, stainless steel, nickel, gold, tin, platinum, nickel-silver alloy (German silver), copper, aluminum, and silver. It should be noted that the conductive material 26 may be vacuum deposited, painted or plated on the surfaces contacting the electrolyte layer 18 of the electrolyte pad 10.

As stated above, the most preferred material for the present embodiment to serve as the electrolyte layer 18 is a conductive adhesive which may include an electrolyte including but not limited to sodium chloride. Accordingly, the most preferred metal is silver as it is compatible with the sodium chloride found in the preferred conductive adhesive. When the sodium chloride of the electrolyte layer 18 and the silver metal, as deposited on the jaws 22 and 24, contact one another, the aforementioned silver/silver chloride system is formed. Alternatively, the deposited silver may be chlorodized with an appropriate chlorodizing agent, such as hypochlorite, to form the silver/silver chloride system. For optimal operation of the electrocardiograph, the metal of choice should not include any other metallic impurities. Therefore, in the preferred embodiment of the invention, the conductive material 26 will comprise a substantially pure silver/silver chloride system.

Figure 3:
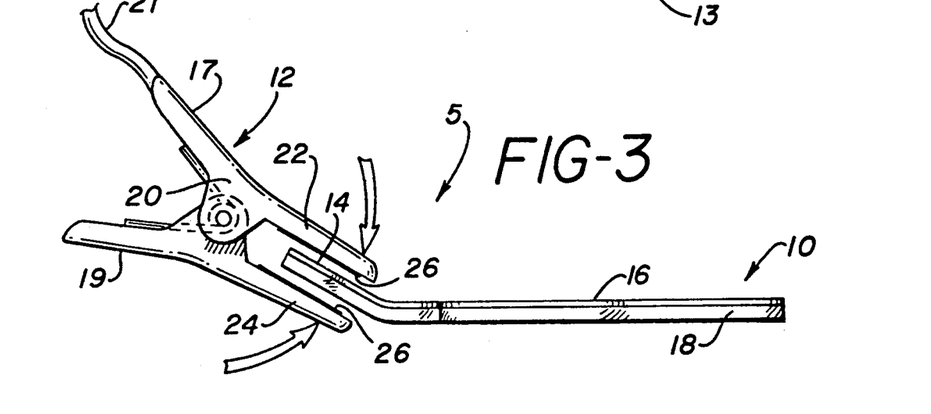
FIG. 3 is a schematic view of the medical electrode assembly depicted in FIG. 1.

Referring now to FIG. 3, a schematic view of the medical electrode assembly 5 is shown. The medical electrode assembly 5 generally comprises the electrolyte pad 10 and the reusable lead wire connector 12. The electrolyte pad 10 includes the backing member 16 being coextensively superposed directly onto the electrolyte layer 18 and the tab 14 extending in a somewhat upwardly direction for receiving the jaws 22 and 24 of the reusable lead wire connector 12. The reusable lead wire connector 12 includes the body 20 having the two jaws 22 and 24 and the conductive material 26. The conductive material 26 preferably comprises at least one metal particle being deposited onto at least one surface of the reusable lead wire connector 12 contacting the electrolyte layer 18. However, when the reusable lead wire connector 12 is configured in substantially an alligator-type or similar clip design, it is preferable to deposit the conductive material 26 on all surfaces which may contact the electrolyte layer 18. Thus, as can be seen in FIG. 3, the reusable lead wire connector 12 includes the conductive material 26 deposited on the inner surface of both jaws 22 and 24. In use, for example, where the medical electrode assembly 5 must be made operational expeditiously by securing the electrolyte pad 10 to the skin of the patient and thereafter, affixing the reusable lead wire connector 12 to the electrolyte pad 10, it is more convenient to have the conductive material 26 deposited on every surface which may contact the electrolyte pad 10. In this way, the possibility of having a surface of the reusable lead wire connector 12 not having the conductive material 26 deposited therein is eliminated.

The reusable lead wire connector 12 illustrated in FIGS. 1 and 3 preferably serves as the sensor or conductor portion of the medical electrode assembly 5 in addition to interconnecting the lead wire between the electrocardiograph and the electrolyte pad 10. Accordingly, the body 20 may comprise a nonconductive binder material with a conductive filler dispersed therein so as to render the reusable lead wire connector 12 conductive. An electrically conductive path is provided for the voltages generated by the heart of the patient through the electrolyte layer 18, the conductive material 26, the jaws 22 and 24, the body 20, the lead wire 21 and terminating at the electrocardiograph which produces the desired diagnostic trace. Preferably, the nonconductive binder material is selected from the group consisting of ethylene vinyl acetate, polyethylene, polypropylene, polyvinylchloride, polytetrafluoroethylene, nylon, silicon rubber, poly(ethylene propylene ethylidene norbornene) and poly(acrylonitrile butadiene styrene) (ABS). The preferable conductive filler is selected from the group consisting of conductive carbons and conductive metals. Most preferably, the nonconductive binder material is either ethylene vinyl acetate (EVA) or poly(acrylonitrile butadiene styrene) (ABS) and the preferred conductive filler is conductive carbon. It will be appreciated by those skilled in the art that other combinations of nonconductive binder materials and conductive fillers may be used in accordance with the invention.

The reusable lead wire connector 12 may have a variety of designs for the set of jaws 22 and 24 that are compatible with the present invention, some of which are illustrated and described more fully below. The reusable lead wire connector 12 serves as the sensor or conductor for the medical electrode assembly 5 and thus, preferably includes a surface having the conductive material 26 deposited thereon which contacts the electrolyte layer 18. It is possible to have a medical electrode assembly 5 which includes a reusable lead wire connector 12 having the body and the conductive material 26 each made from dissimilar metals. Although this configuration is operational in accordance with the present invention, the preferred reusable lead wire connector 12 includes the jaws 22 and 24 each made from a nonconductive binder material rendered conductive by the inclusion of a conductive filler dispersed therein. A regular trace having a more stable base line is produced with the preferred reusable lead wire connector 12.

Figure 4:
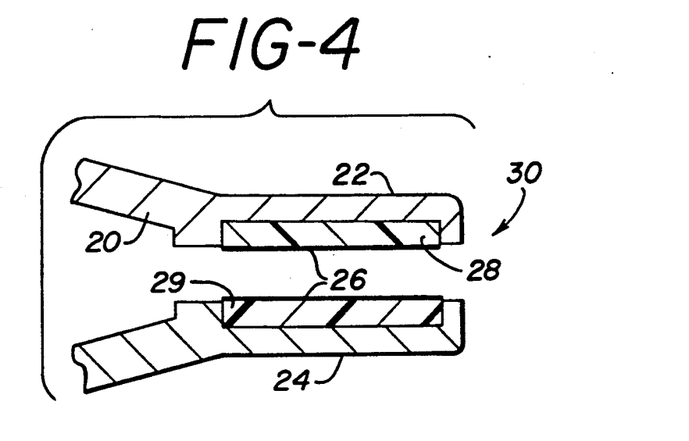
FIG. 4 is a partial schematic view of a reusable lead wire connector having an insert contained within each jaw.

Referring now to FIG. 4, a partial schematic of a reusable lead wire connector 30 is illustrated. The reusable lead wire connector 30 may be used in accordance with the medical electrode assembly 5 as illustrated and described in FIGS. 1 and 2. The reusable lead wire connector 30 includes the body 20 and the jaws 22 and 24 as described with regard to the reusable lead wire connector 12. However, each of the jaws 22 and 24 have a recess for receiving a pair of inserts 28 and 29. The body 20 preferably comprises a nonconductive binder material including but not limited to ethylene vinyl acetate, polyethylene, polypropylene, polyvinylchloride, polytetrafluoroethylene, nylon, silicon rubber, poly(ethylene propylene ethylidene norbornene) and poly(acrylonitrile butadiene styrene). The inserts 28 and 29 comprise a nonconductive binder material as described above, and a conductive filler dispersed therein. The conductive filler may comprise any of those materials described above with regard to the reusable lead wire connector 12. The reusable lead wire connector 30 includes the conductive material 26 deposited on the surfaces of the inserts 28 and 29. It should be understood that only one surface must have the conductive material 26 deposited thereon, but in the interest of convenience, it is preferable to have both surfaces coated therewith.

Figure 5:
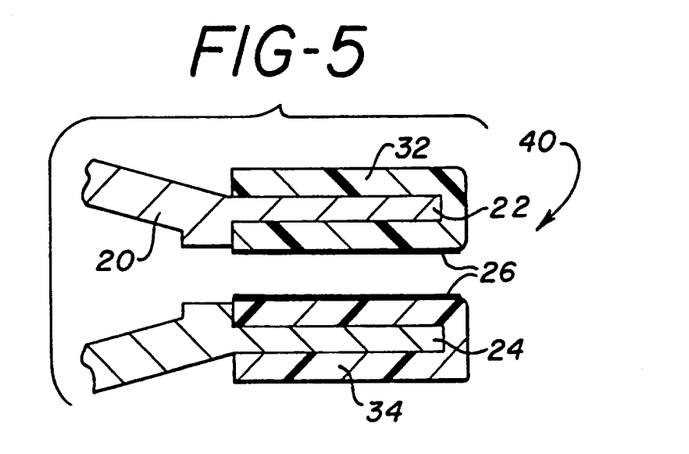
FIG. 5 is a partial schematic view of a reusable lead wire connector having a sleeve fitted over each jaw

Referring now to FIG. 5, a reusable lead wire connector 40 similar to the reusable lead wire connector 12 illustrated FIG. 1 and 3 is shown. The reusable lead wire connector 40 may be used in accordance with the invention as described above. The jaws 22 and 24 have sleeves, 32 and 34 respectively, which fit over each jaw 22 and 24 of the reusable lead wire connector 40. The body 20 preferably comprises a conductive material, such as a metal, and the sleeves 32 and 34 preferably comprise a nonconductive binder material having a conductive filler dispersed therein. However, the body 20 of the reusable lead wire connector 40 may comprise a nonconductive binder material as described above. The nonconductive binder material and the conductive filler may include those materials described above in addition to others known in the art. The conductive material 26 comprising at least one metal particle is deposited on the inner surfaces of the sleeves 32 and 34 such that it will contact the electrolyte layer 18 of the electrolyte pad 10.

Figure 6:
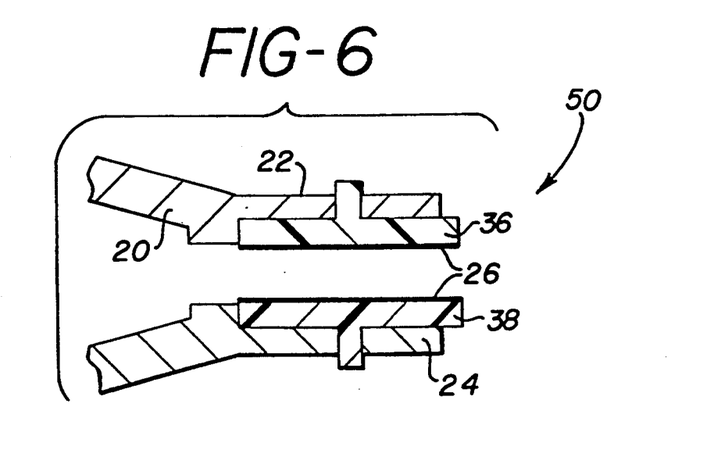
FIG. 6 is a partial schematic view of a reusable lead wire connector having a T-shaped inserts.

Yet another reusable lead wire connector 50 which may be used in accordance with the invention is illustrated in FIG. 6. The reusable lead wire connector 50 includes the two jaws 22 and 24 and the body 20 generally having an alligator-type design. The body 20, including jaws 22 and 24, may comprise a conductive material such as a metal or a nonconductive binder material including but not limited to those described above. The jaws 22 and 24 include a recess for receiving T-shaped inserts 36 and 38, respectively. The T-shaped inserts 36 and 38 preferably comprise a nonconductive binder material having a conductive filler dispersed therein. The preferred combination comprises an ABS material having a conductive carbon dispersed therein so as to render the T-shaped inserts 36 and 38 conductive. The reusable lead wire connector 50 includes the conductive material 26 deposited on the surface of each T-shaped inserts 36 and 38. The inner surfaces of the T-shaped inserts 36 and 38 contact the electrolyte layer 18 of the electrolyte pad 10. The preferable conductive material 26 comprises at least one metal particle. Most preferably, the silver/silver chloride system serves as the conductive material 26.

Figure 7:
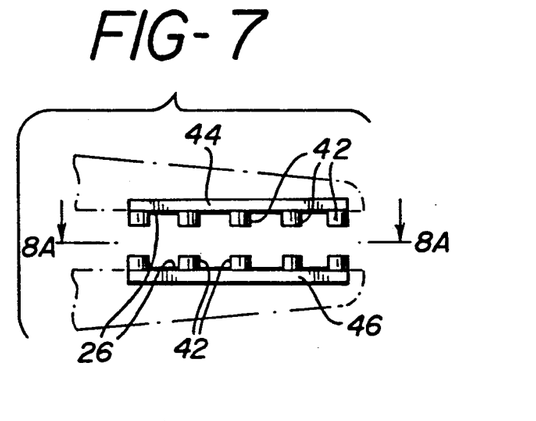
FIG. 7 is a schematic view of a pair of inserts having a series of bumps which may be used with the reusable lead wire connector in accordance with the invention.
Figure 8:
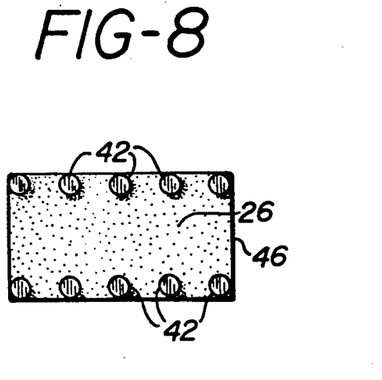
FIG. 8 is a top view of an insert shown in FIG. 7 taken along line 8A—8A.

FIGS. 7 shows a partial schematic view of two inserts 44 and 46, respectively, for the reusable lead wire connector 12 according to the invention. FIG. 8 illustrates a view taken along line 8A—8A in FIG. 7. The inserts 44 and 46 may be used with the reusable lead wire connectors illustrated and described herein, or may be incorporated into any other reusable lead wire connector having a design compatible with the present invention. Typically, the electrolyte layer 18 of the electrolyte pad 10 will comprise a relatively soft material which is susceptible to being compressed into an extremely thin layer by the reusable lead wire connector 12. The result is an increase in the interface impedance which interferes with the optimal operation of the medical electrode assembly 5. In an effort to eliminate this problem, the inserts 44 and 46 include a series of bumps 42 which may have a multitude of shapes and sizes depending upon the particular reusable lead wire connector 12 used. For example, the bumps 42 in FIGS. 7 and 8 have an annular, column shape and are linearly spaced at the sides of inserts 44 and 46. However, it should be appreciated that the bumps 42 may have a square shape, a pyramidical shape or any other shape resembling a bump, ridge, mesa, pillar, tooth or other surface irregularity. The conductive material 26 is deposited onto the surface of inserts 44 and 46.

Figure 9:
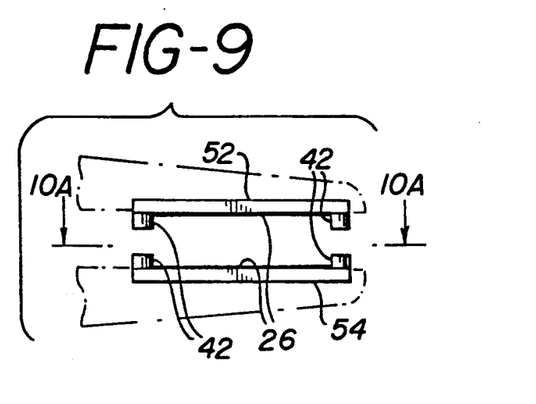
FIG. 9 is a schematic view of a pair of inserts having four bumps positioned at each corner of each insert which may be used with the reusable lead wire connector according to the invention.
Figure 10:
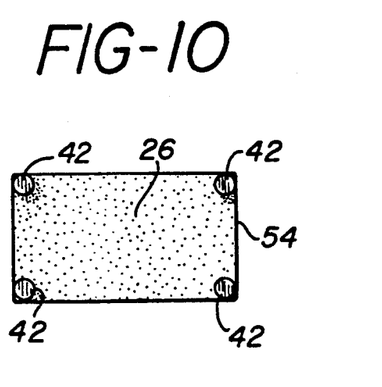
FIG. 10 is a top view of an insert shown in FIG. 9 taken along line 10A—10A.

Referring now to FIG. 9, another set of inserts 52 and 54 which may be used with the reusable lead wire connector 12 are shown. FIG. 10 is a view taken along the line 10A—10A in FIG. 9. The inserts 52 and 54 include four bumps 42 positioned at each corner thereof such that they face one another. The bumps 42 illustrated in FIGS. 9 and 10 have an annular, column shape, similar to a pillar. However, the bumps 42 may have other shapes in addition to those described herein. As with inserts 44 and 46, the conductive material 26 is deposited on the surface of each insert 52 and 54, respectively, and between the bumps 42. Accordingly, when the inserts 52 and 54 are compressed together to contact the electrolyte layer 18 of the electrolyte pad 10, the electrolyte layer 18 maintains a relatively uniform thickness. Thus, the inserts 52 and 54 prevent any increase in the interface impedance as a result of having the reusable lead wire connector 12 affixed to the electrolyte pad 10.

Figure 11:
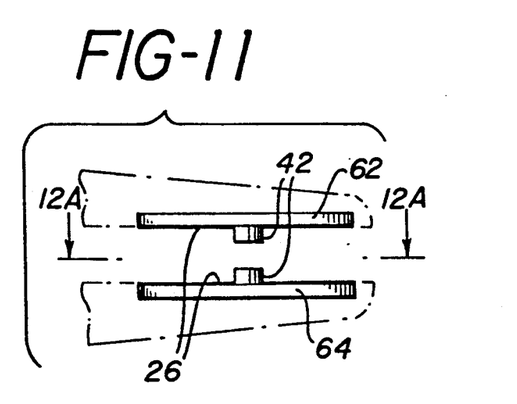
FIG. 11 is a schematic view of yet another pair of inserts which may used with the reusable lead wire connector in accordance with the invention.
Figure 12:
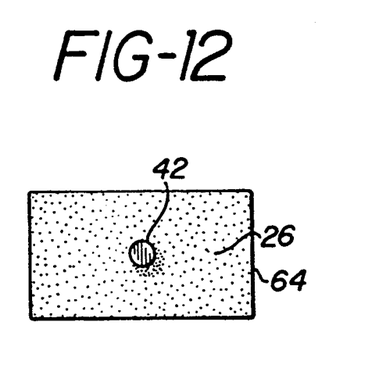
FIG. 12 is a top view of an insert shown in FIG. 11 taken along line 12A—12A.

FIGS. 11 and 12 illustrate yet another configuration for a pair of inserts 62 and 64 used in conjunction with the reusable lead wire connector 12 of the present invention. The pair of inserts 62 and 64 include a single bump 42 positioned at the center thereof such that each bump 42 faces one another. The conductive material 26 is deposited over the inner surface of each insert 62 and 64, respectively. When the inserts 62 and 64 are compressed together, each bump 42 is compressed together against the tab 14 of the electrolyte pad 10. This sufficiently secures the reusable lead wire connector 12 to the electrolyte pad 10 yet maintains a uniform thickness of the electrolyte layer 18 so as to minimize the interface impedance.

Figure 13:
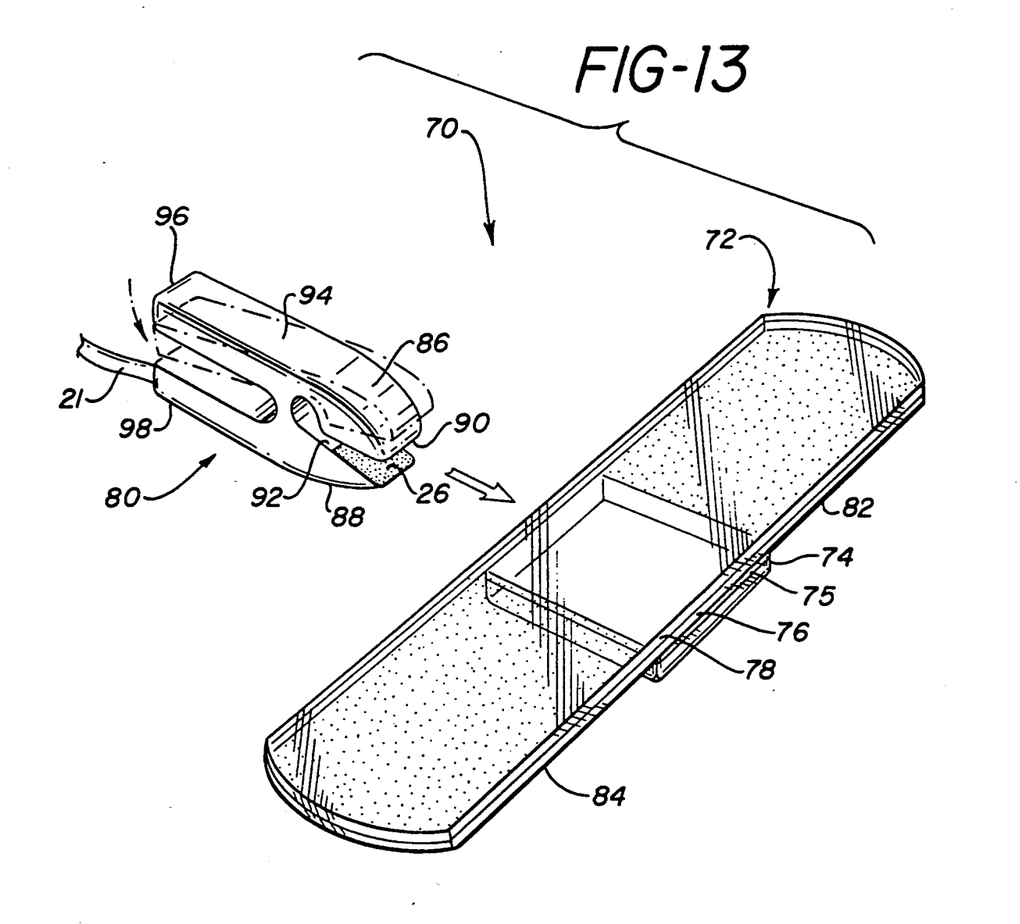
FIG. 13 is a perspective view of yet another medical electrode assembly especially suitable for long-term monitoring.

Referring now to FIG. 13, a medical assembly 70 especially suitable for long-term electrocardiograph monitoring of a patient is illustrated. The medical assembly 70 includes a long-term electrolyte pad 72 resembling a bandage or the like and a reusable lead wire connector 80. The electrolyte pad 72 is used in conjunction with the reusable lead wire connector 80 both of which have the same function as the electrolyte pad 10 and the reusable lead wire connector 12, respectively. The electrolyte pad 72 generally comprises an electrolyte layer 74, a support layer 75, an adhesive layer 76 and a backing member 78.

The backing member 78 is coextensively superposed directly onto the adhesive layer 76. The backing member 78 and the adhesive layer 76, together, are disposed over the support layer 75 and the electrolyte layer 74. The backing member 78 and the adhesive layer 76, together, include a first portion 82 extending in a first direction and a second portion 84 extending in a second direction, which is diametrically opposite to the first direction, such that the electrolyte pad 72 substantially resembles a bandage-like structure. Both the first portion 82 and the second portion 84 extend beyond the support layer 75 and the electrolyte layer 74 such that the adhesive layer 76 of the first portion 82 and the second portion 84 may be secured to the skin of the patient. It should be understood that the backing member 78 and the adhesive layer 76, together, may include a portion having any shape or size so long as the portion secures the electrolyte pad 72 firmly to the patient's skin sufficient for long-term monitoring. Thus, one skilled in the art may devise an electrolyte pad suitable for long-term monitoring, yet does not include the first portion 82 or the second portion 84 without departing from the scope of the invention.

The adhesive layer 76 preferably comprises any known "patient contact" adhesive which is compatible with the patient's skin. The electrolyte layer 74 is preferably formed from any of those materials discussed above in regard to the electrolyte layer 18. With regard to the support layer 75, it is disposed over the electrolyte layer 74 to provide additional support. However, the support layer 75 may be excluded from the electrolyte pad 72 without departing from the scope of the invention. When used, the support layer 75 is preferably formed of a polymeric material including but not limited to polyvinylchloride, and other plastics. Such a polymeric material may be vapor permeable and/or liquid permeable. The backing member 78 is preferably made from a nonconductive material such as those described with reference to backing member 16 illustrated in FIG. 1. Additionally, the electrolyte pad 72 may have a carrier sheet or release sheet (not shown) for protecting the entire undersurface of the electrolyte pad 72 prior to use. The material used for such a carrier sheet may be any of the types widely known in the art which exhibit little or no tendency to adhere to the adhesive layer 76 and the electrolyte layer 74 with which it is in contact. Such characteristics are usually attributed to protective coatings deposited on the carrier sheet. The carrier sheet may be scored or perforated to permit easy removal from the undersurface of the electrolyte pad 72. Similar carrier sheets may be used with the other embodiments of the invention.

The reusable lead wire connector 80 used in the medical assembly 70 may also be used with the electrolyte pad 10 shown in FIG. 1 in addition to the electrolyte pad 11 shown in FIG. 2. The reusable lead wire connector 80 comprises a set of jaws 86 and 88 each having an inner surface 90 and 92, respectively, for contacting the electrolyte pad 72. The jaws 86 and 88 are configured in a substantially alligator-type clip 94 having the lead wire 21 connected thereto. The inner surfaces 90 and 92 of the jaws 86 and 88, respectively, are spaced apart at a predetermined distance to facilitate affixing the jaws 86 and 88 to the electrolyte pad 72 without having to compress the jaws 86 and 88 together. In a typical alligator-type clip, the inner surfaces 90 and 92 of the jaws 86 and 88 contact one another while the alligator-type clip is in its natural or resting position.

Conventionally, the alligator-type clip 94 will have handles 96 and 98 which may be compressed together, thereby spreading the jaws 86 and 88 apart which allows the reusable lead wire connector 80 to be affixed to the electrolyte pad 72. The reusable lead wire connector 80 is then allowed to return to its natural or resting position which may allow the jaws 86 and 88 to compress the electrolyte pad 72 excessively, thereby increasing the interface impedance between the electrolyte pad 72 and the reusable lead wire connector 80. As discussed above, the reusable lead wire connector designs shown in FIGS. 4–12 eliminate or minimize such an increase in interface impedance. Similarly, the reusable lead wire connector 80 minimizes any increase in interface impedance by maintaining the jaws 86 and 88 apart from one another at a predetermined distance. The predetermined distance may be substantially the same as the thickness of the electrolyte pad 72 or slightly smaller since the handles 96 and 98 may be compressed together to facilitate affixing the jaws 86 and 88 to the electrolyte pad 72.

The reusable lead wire connector 80 further includes the metallic conductive material 26, as described above, superposed directly onto the inner surfaces 90 and 92 of the jaws 86 and 88, respectively. Preferably, the metallic conductive material 26 comprises at least one metal particle selected from the group consisting of titanium, stainless steel, nickel, gold, tin, platinum, nickel-silver alloy, copper, aluminum and silver. As with the embodiments discussed above, the metal of choice will be compatible with the electrolyte layer 74 material. In that regard, the preferable metallic conductive material 26 comprises the aforementioned silver/silver chloride system which is compatible with the conductive adhesive material of the electrolyte layer 74. Preferably, the reusable lead wire connector 80 is made from a nonconductive binder material having a conductive filler dispersed therein. The nonconductive binder and the conductive filler preferably comprise those materials described with reference to the reusable lead wire connector 12 of FIG. 1.

Having thus describe the invention in detail by way of reference to preferred embodiments thereof, it will be apparent that other modifications and variations are possible without departing from the scope of the invention defined in the appended claims. For example, the reusable lead wire connector may have design configurations which depart from those described herein with reference to the reusable lead wire connector 12.

What is claimed is:

1. A medical electrode assembly for an electrocardiograph comprising:
   an electrolyte pad including an electrolyte layer which may be secured to the skin of a patient; and a backing member made from a nonconductive material being continuously and coextensively superimposed directly onto said electrolyte layer; said backing member and said electrolyte layer having a tab; and a reusable lead wire connector including a set of jaws configured in substantially an alligator-type clip, each of said jaws having an inner surface which may be compressed together for contacting said tab of said electrolyte pad such that electrocardiographic voltages generated by a patient are transmitted through said electrolyte layer and said inner surface of at least one of said jaws to said electrocardiograph, wherein said inner surface of each said jaw includes an insert made from a nonconductive binder material having a conductive filler dispersed therein; and at least one metal particle superposed directly onto the inner surface of said jaws.

2. The assembly of claim 1 wherein the surface of said insert includes at least one bump to maintain the thickness of said electrolyte pad.

3. A medical assembly for long-term electrocardiograph monitoring comprising:

an electrolyte pad including an electrolyte layer which may be secured to the skin of a patient; and a backing member made from a nonconductive material being continuously and coextensively superposed over said electrolyte layer wherein said backing member includes a portion extending beyond said electrolyte layer for securing said electrolyte layer to the skin of a patient; and a reusable lead wire connector including a set of jaws each having an inner surface for contacting an electrolyte pad, said jaws are formed from a nonconductive binder material having a conductive filler dispersed therein and are configured in substantially an alligator-type clip having a lead wire connected thereto, said jaws are spaced apart at a predetermined distance to facilitate affixing said jaws to said electrolyte pad without having to compress said jaws together; and at least one metal particle superposed directly onto the inner surface of said jaws.

* * * * *

UNITED STATES PATENT AND TRADEMARK OFFICE
CERTIFICATE OF CORRECTION

PATENT NO. : 5,195,523
DATED      : March 23, 1993
INVENTOR(S) : James V. Cartmell, et al It is certified that error appears in the above-identified patent and that said Letters Patent is hereby corrected as shown below:

Col. 13, Line 5  "coextensively superimposed" should be --coextensively superposed--.

Signed and Sealed this

Eighteenth Day of January, 1994

Attest:

BRUCE LEHMAN

Attesting Officer         Commissioner of Patents and Trademarks